(12) United States Patent
Burton (10) Patent No.: US 8,281,787 B2
(45) Date of Patent: Oct. 9, 2012

(54) BIO-MASK WITH INTEGRAL SENSORS

(75) Inventor: David Burton, Victoria (AU)

(73) Assignee: Compumedics Limited, Abbotsford (AU)

( * ) Notice: Subject to any disclaimer, the term of this patent is extended or adjusted under 35 U.S.C. 154(b) by 252 days.

(21) Appl. No.: 12/638,891

(22) Filed: Dec. 15, 2009

(65) Prior Publication Data

US 2010/0147304 A1   Jun. 17, 2010

Related U.S. Application Data

(63) Continuation of application No. 10/777,572, filed on Feb. 11, 2004, now abandoned, which is a continuation-in-part of application No. 09/465,054, filed on Dec. 16, 1999, now Pat. No. 7,204,250.

(51) Int. Cl.
*A62B 7/00* (2006.01)
*A61M 16/00* (2006.01)

(52) U.S. Cl. ......... 128/204.23; 128/204.21; 128/204.18; 128/200.24

(58) Field of Classification Search ............. 128/207.11, 128/206.21, 204.21, 206.12, 205.23, 206.27, 128/206.28; 600/508, 529, 537, 538, 545, 600/534, 544
See application file for complete search history.

(56) References Cited

U.S. PATENT DOCUMENTS

| | | | |
|---|---|---|---|
| 3,606,881 A | 5/1967 | Woodson | |
| 4,875,477 A | 10/1989 | Waschke et al. | |
| H1039 H * | 4/1992 | Tripp et al. | 128/206.28 |
| 5,131,399 A | 7/1992 | Sciarra | |
| 5,134,995 A | 8/1992 | Gruenke et al. | |
| 5,199,424 A | 4/1993 | Sullivan et al. | |
| 5,243,971 A | 9/1993 | Sullivan et al. | |
| 5,293,867 A | 3/1994 | Oommen | |
| 5,353,788 A | 10/1994 | Miles | |
| 5,353,793 A | 10/1994 | Bornn | |
| 5,411,527 A * | 5/1995 | Alt | 607/5 |
| 5,435,316 A * | 7/1995 | Kruse | 600/510 |
| 5,503,146 A | 4/1996 | Froehlich et al. | |

(Continued)

FOREIGN PATENT DOCUMENTS

GB   2294642   5/1996

(Continued)

OTHER PUBLICATIONS

Jamison, et al., "Wireless Electroencephalogram", https://courses.cit.cornell.edu/bionb440/FinalProjects/f2005/kwj5/, Fall 2005.

*Primary Examiner* — Annette Dixon
(74) *Attorney, Agent, or Firm* — Briggs and Morgan, P.A.; John F. Klos; Audrey J. Babcock (57) ABSTRACT

A system including a mask to detect an EEG signal and to deliver a gas, the mask having a forehead support extending from the body and adapted to contact a forehead surface of the patient during use, the forehead support having a plurality of sensors located thereon for detecting electrophysiological signals of the patient, with the plurality of sensors including EEG sensors positioned proximate to FP1/FP2 standard electrode placement positions of the patient, a gas delivery device in fluid communication with the mask and having an adjustable gas output, and a control system for determining a sleep stage from EEG signals detected by the mask and adjusting a gas delivery device based on the sleep stage.

21 Claims, 7 Drawing Sheets

U.S. PATENT DOCUMENTS

| | | | |
|---|---|---|---|
| 5,503,147 | A | 4/1996 | Bertheau |
| 5,507,716 | A | 4/1996 | LaBerge et al. |
| 5,584,296 | A | 12/1996 | Cui et al. |
| 5,617,849 | A | 4/1997 | Springett et al. |
| 5,673,692 | A | 10/1997 | Schulze et al. |
| 5,860,417 | A | 1/1999 | Kettl et al. |
| 6,000,395 | A | 12/1999 | Brown |
| 6,029,665 | A | 2/2000 | Berthon-Jones |
| 6,032,065 | A * | 2/2000 | Brown .................. 600/383 |
| 6,097,981 | A | 8/2000 | Freer |
| 6,119,693 | A | 9/2000 | Kwok et al. |
| 6,171,258 | B1 * | 1/2001 | Karakasoglu et al. ........ 600/529 |
| 6,199,550 | B1 * | 3/2001 | Wiesmann et al. ...... 128/204.23 |
| 6,240,921 | B1 | 6/2001 | Brydon et al. |
| 6,357,440 | B1 | 3/2002 | Hansen et al. |
| 6,385,486 | B1 | 5/2002 | John et al. |
| 6,397,845 | B1 | 6/2002 | Burton |
| 6,398,739 | B1 | 6/2002 | Sullivan et al. |
| D468,421 | S | 1/2003 | Smart |
| D468,823 | S | 1/2003 | Smart |
| 6,532,961 | B1 | 3/2003 | Kwok et al. |
| 6,542,081 | B2 | 4/2003 | Torch |
| D476,732 | S | 7/2003 | Smart |
| 6,635,021 | B1 | 10/2003 | Sullivan et al. |
| 6,708,051 | B1 | 3/2004 | Durousseau |
| 7,054,680 | B1 | 5/2006 | Genger et al. |
| 7,204,250 | B1 | 4/2007 | Burton |
| 2004/0144383 | A1 | 7/2004 | Thomas et al. |
| 2005/0268916 | A1 | 12/2005 | Mumfort et al. |
| 2007/0208269 | A1 | 9/2007 | Mumford et al. |
| 2008/0092898 | A1 | 4/2008 | Schneider et al. |
| 2008/0127978 | A1 | 6/2008 | Rubin et al. |

FOREIGN PATENT DOCUMENTS

| | | |
|---|---|---|
| WO | WO-9716216 | 5/1997 |
| WO | WO-9733641 | 9/1997 |
| WO | WO-0066209 | 11/2000 |

* cited by examiner

BIO-MASK WITH INTEGRAL SENSORS

RELATED APPLICATIONS

This application is a continuation of U.S. Ser. No. 10/777,572, filed Feb. 11, 2004, now abandoned, which was a continuation-in-part of U.S. Ser. No. 09/465,054, filed Dec. 16, 1999, now U.S. Pat. No. 7,204,250, each application being incorporated by reference herein.

BACKGROUND OF THE INVENTION

1. Field of the Invention

This invention relates to a breathing mask with built in sensors for monitoring patients with sleep apnea, breathing disorders for use during anesthesia or ventilation support.

2. Description of the Related Art

Masks such as shown in U.S. Pat. No. 5,243,971 for applying a positive pressure to patients with apnea and other breathing disorders have been developed. These masks provide seals for preventing air from escaping from the mask at the junction of the mask and face. Other types of masks for gas delivery to a patient are also in common use.

Measuring air flows to a patient has been accomplished by metering sensors in the air supply connected to the mask as in U.S. Pat. No. 5,503,146 or by belts around the patients chest to measure his breathing as in U.S. Pat. No. 5,131,399.

Some devices such as in U.S. Pat. No. 5,507,716 provide sensors combined with sleep masks for covering the eyes of a patient. However there is no known example of sensors built into breathing masks for monitoring or studying patients with breathing disorders.

Currently if a patient is to be carefully monitored a plurality of electrodes or sensors would have to be individually applied to the patient and wired to recording equipment. The plurality of sensors and tangle of ensuing wires impede the usage of such monitoring equipment. Sensors providing useful information include Electra-encephalogram (EEG), electromyography (EMG), electro-oculogram (EOG), electro-cardiogram (ECG), Pulse Transit Time (PTT), gas flow sensors, temperature sensors, microphones, blood oxygen meters, blood pressure sensors, pulse sensors, patient movement, position, light, activity sensors, mask leakage, mask pressure, eye movement by polyvinylidene flouride-(PVD) or Piezo, and other means of gathering data about the patient or his environment.

It is very inconvenient for the patient and the health care worker to attach a series of different devices to a patient to monitor a plurality of different parameters simultaneously. Therefore a single device for easily measuring a plurality of parameters is desired.

SUMMARY OF THE INVENTION

The invention relates to providing sensors in breathing masks to make it easy to monitor a patient. The mask has a soft pliable seal material around its perimeter in contact with the patient's face to form a secure seal therewith. Sensors may be recessed into the soft pliable seal material at the surface for contact with the skin of the user when the mask is applied to the user's face. The wiring for the sensors may be inside the soft pliable seal material insulating the wires from damage during use of the mask. Many sensors can be incorporated into the mask. Sensors may be placed on the perimeter or on other portions of the mask not in contact with the skin. Sensors may also be placed on straps or caps used in conjunction with the masks or on other devices used with the mask.

Monitoring of patients with sleep disorders, breathing disorders or for anesthesia is made easier and more convenient for the patient and for the health care provider since all the sensors needed are built into a mask which is easily and quickly placed on the patient with all the wiring to the sensors integral with the mask and accessed by a single plug.

The types of sensors on or in the mask and straps or caps connected to the mask include but are not limited to oximetery sensors, patient position sensors, eye movement sensors, leak detection sensors, EEG, EMG, EOG, ECG, PTT, microphones, pulse, blood pressure, oxygen saturation, temperature, movement sensors, position sensors, light sensors, leak detection sensors and gas delivery sensors.

Connections to outside sources of gases delivered to the mask are by a gas nozzle hook up on the mask. A connection to electrical power and data output cables are by a plug in to a cable connecting to the mask. Alternatively batteries in the mask and telemetry equipment in the mask can provide power and transmission of the data to a microprocessor or computer. For portability the microprocessor can be attached to the mask or be carried by the patient. Similarly a bottle of gas may be connected to the mask and carried by the patient to allow mobility of the patient while wearing the mask.

Unique applications for the bio-mask include the capability to apply anesthesia-depth monitoring while administering anesthesia gas to a subject. The ability to monitor the patient non-invasively with the bio-mask while at the same time administering the anesthesia gas to the patient provides a bio-feedback function for immediate and responsive anesthesia depth of the subject. The bio-mask can be used to determine the subject's sleep state by applying standard sleep staging criteria, such as that of R&K rules and/or the application of diagnostic techniques which analyze a number of EEG signals, such as Bispectral Analysis. The invention is unique in its capability to apply such analysis with the minimal-invasive application of a subject breathing mask.

R&K rules refer to "A Manual of Standardized Terminology, Techniques and Scoring System for Sleep Stages of Human Subject" by Rechtschaffen and Anthony Kales, Editors 1968 which is hereby made a part hereof and incorporated herein by reference.

Another unique application for the bio-mask includes the combination of the bio-mask with a cardiac pacemaker. It is envisioned that the gas delivery to the No-mask may be controlled, in part, via communication from a pacemaker to a bio-mask controller.

DESCRIPTION OF THE PREFERRED EMBODIMENTS

Figure 1:
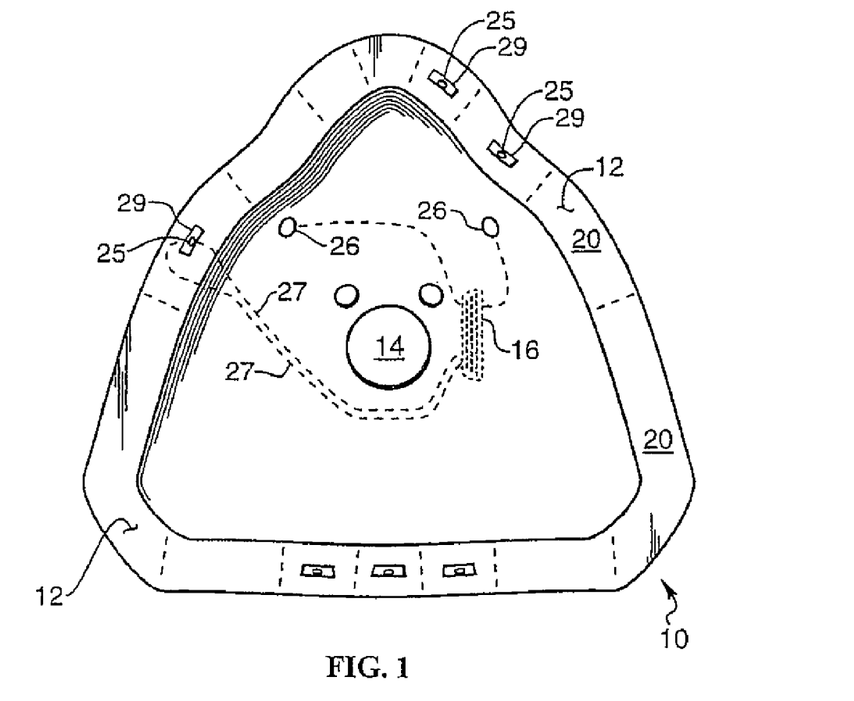
FIG. 1 shows a schematic view of the zones for sensors on the inside surface of a soft pliable material on the perimeter of the breathing mask.

FIG. 1 shows the inside of mask 10 including the perimeter surface 12 which contacts the patient's face. The perimeter surface 12 has a plurality of zones 20. Each zone 20 having a sensor 25 in a recess 29 for measuring a parameter of the patient to be monitored or other data such as gas leakage. Other sensors 26 are on the mask 10 but not in contact with the patient's skin. These sensors 26 measure patient data or related data such as ambient light, gas pressure in the mask or ambient temperature.

The mask 10 has a gas connector 14 for connecting a hose 32 to provide a gas to the mask 10 and a mask interface connector 16 for plugging in a cable 30 for a power supply and for data transmission In some embodiments of the invention the sensors 25 do not require an outside source of power as the sensors such as heat sensors and light sensors generate current. The mask perimeter surface 12 is preferably made out of a soft pliable material such as silicone rubber for making a good sealing contact with the face of the patient to prevent gas leakage. The material should be soft and pliable enough to follow the contours of the face. The perimeter surface preferably has recesses 29 on the surface for the insertion of sensors 25 so that the sensors can make contact with the patient's skin when the mask is pressed against the patient's face.

Figure 2:
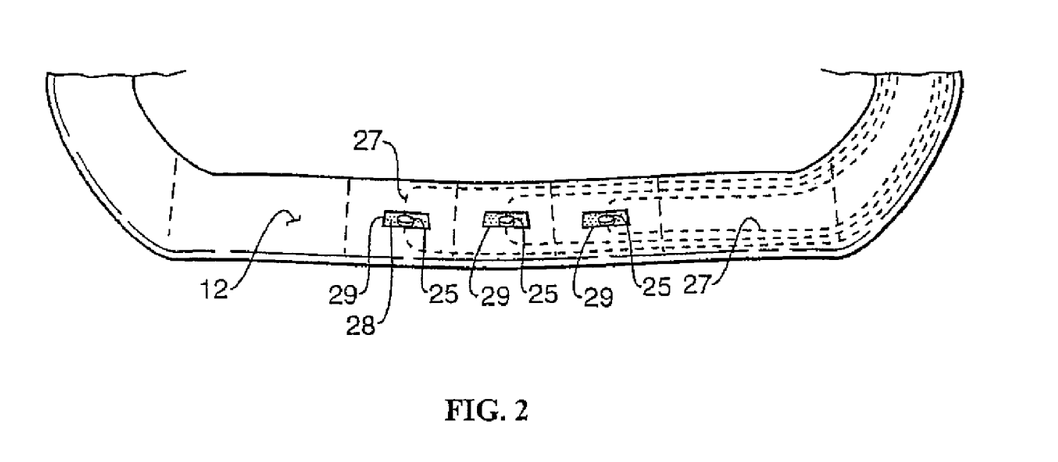
FIG. 2 shows a view of the sensors and wiring inside the soft pliable material on the perimeter of the breathing mask.
Figure 3:
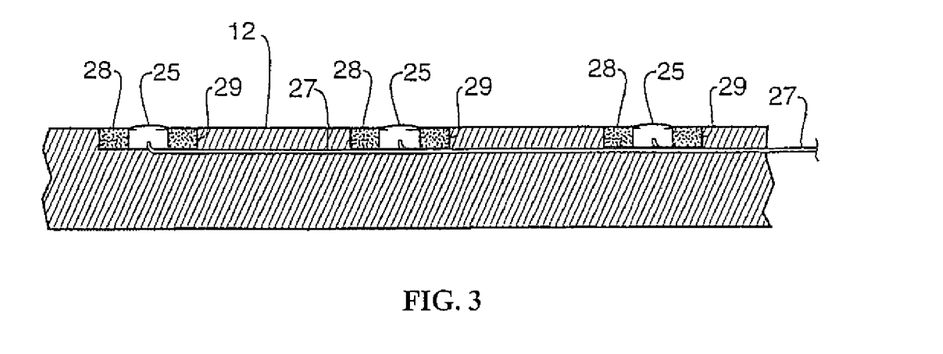
FIG. 3 shows a side schematic view of the sensors and the wiring inside of the soft pliable material on the perimeter of the breathing mask.

As seen in FIG. 3 a sensor or electrode 25 attachment to the mask 10 preferably utilizes a rubber compound 28 such as silicon or other medical grade type rubber embedded with carbon or other conductive materials for electrical contact of skin to the mask. As shown in FIG. 2 the recesses 29 are large enough to accommodate electrical connections to leads 27 which are buried in the soft pliable material under the perimeter surface 12. The leads 27 are thus protected from damage and electrically insulated. Preferably the sensors 25 will plug into the leads 27 or printed circuits in the recesses 29. The leads 27 are preferably on printed circuits embedded in the mask or fine wires embedded in the mask and connect the sensors 25 to the mask interface connector 16.

Figure 5:
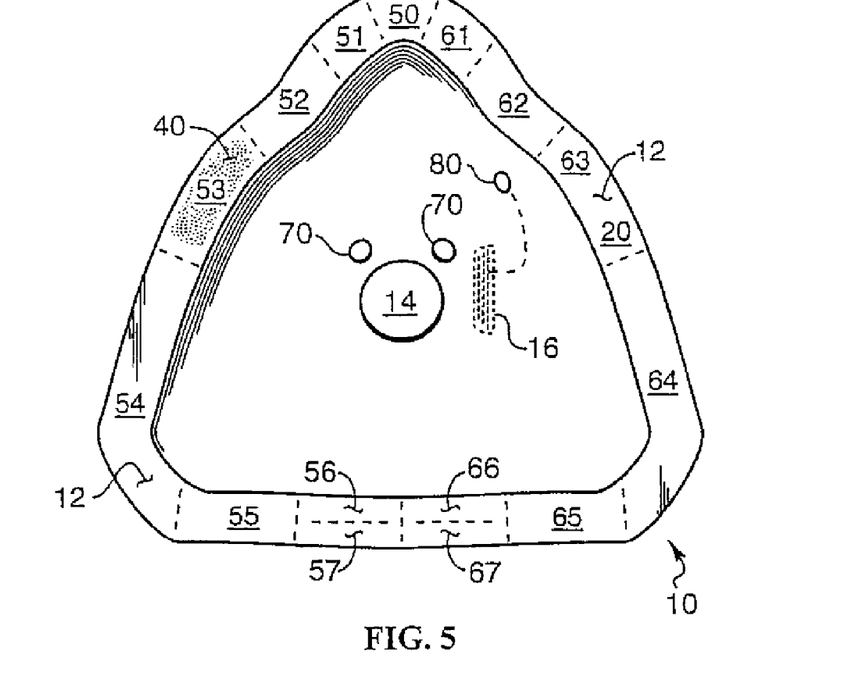
FIG. 5 shows a schematic view of the sensor zones on the perimeter of the breathing mask.

FIG. 5 shows conductive material 40 on the surface in zones 20, such as carbon embedded silicon, can be used on the surface of the perimeter 12 of mask 10 in separate zones 20 to conduct the electrical surface energy from the patient's face. The conductive material 40 is preferably moisture activated to improve electrical conductivity when in contact with the skin. The conductive material 40 may be utilized for some or all electrode 25 contacts in the zones. Alternatively electrodes 25 may directly contact the patient's face. The electrodes may also be inside of the soft pliable material on the perimeter 12 of the mask 10.

Figure 4:
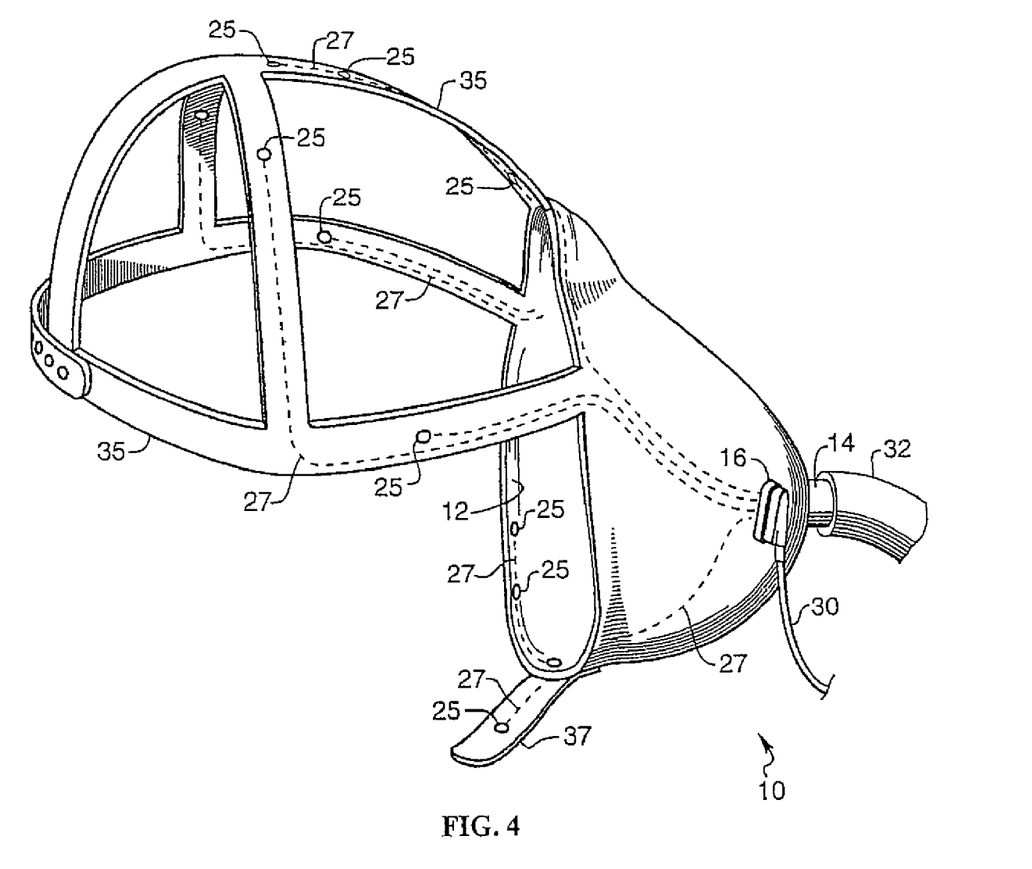
FIG. 4 shows a side schematic view of the straps connected to the mask with sensors embedded in the straps and the mask.

FIG. 4 shows a side view of the mask 10 and straps 35 used to keep the mask in place on a patient. The straps 35 have sensors 25 connected to leads 27, which connect the sensors to the mask interface connector 16 and to cable 30 for transmitting data to a computer or other device. The sensors 25 in the straps 35 may be electro-encephalogram EEG sensors for measuring brain waves. The straps 35 may be replaced with a cap having sensors therein. Alternatively a chin strap 37 may be used having sensors 25.

FIG. 5 shows an example of the types of sensors 25 used in zones 20 around the perimeter of the mask 10. Physiological signals from a patient's skin potential are detected by sensors in the zones 20 around perimeter 12 of mask 10. Conductive electrode paste 40 may be used to improve the electrical contact between the sensors 25 and the surface of the skin. The conductive paste 40 can assist in reducing the impedance between the face and the electrical output from the sensors 25 in zones 20. The conductive paste 40 may also assist in preventing gas leaks.

As an example of a mask sensor layout the following sensors and their functions are described. However many other types of sensors and arrangements of the sensors are possible.

Zone 50 is an electro-oculogram (EOG) to obtain electrical eye movement reference signals from over the bridge of the nose.

Zone 51 is an EOG to detect electrical eye movement signals for the inner left eye and zone 61 is designated for electrical eye movement signals for the inner right eye. Eye movement data is related to stages of sleep such as rapid eye movement REM, which indicates a deep sleep state and dreaming.

Zone 52 is designated for an EOG to detect electrical eye movement signals for the outer left eye and zone 62 is designated for electrical eye movement signals for the outer right eye.

Zone 53 is designated for electro-myography (EMG) to detect electrical signals from muscle contractions in the upper left chin. Zone 63 is correspondingly for the upper right chin. Zones 54 and 64 are for the lower left and lower right chin respectively. The amplitude of the chin signals is proportional to the relaxation state and subsequent sleep state of the patient.

Zone 55 is the EMG for the upper left lip, giving information about sleep stages. It is proportional to the relaxation and sleep states of the patient. Zone 65 is the EMG for the upper right lip.

Zone 56 is the EMG for the left nasal inner mask it also provides signals for the lip movements and is proportional to the relaxation and sleep states of the patient. Similarly zone 66 is for the right nasal inner mask EMG.

Zones 57 and 67 are for the oral left and oral right outer mask EMG signals which are also proportional to the relaxation and sleep states of the patient.

Zone 70 is for pressure sensor ports for airflow determination.

Microphone 80 on the mask detects the patient's breathing or snoring sounds.

Figure 6:
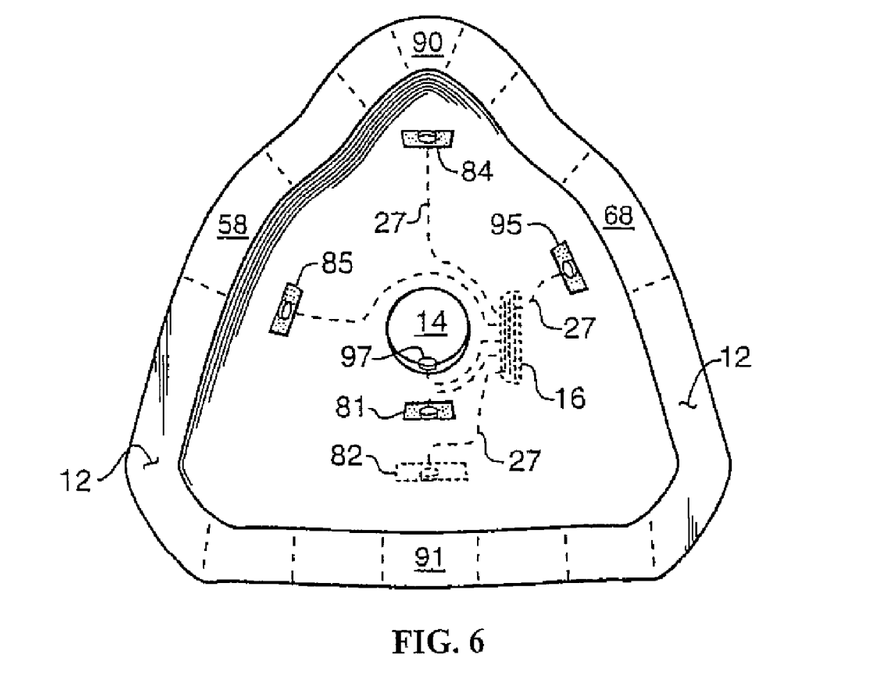
FIG. 6 shows a schematic view of the sensors on the inside surface of a breathing mask.

FIG. 6 shows an alternate embodiment where two sensors 58 and 68 are used to find the patient's electrocardiogram ECG. This data is also useful for monitoring a patient. The patient's heart functions provide a lot of useful data about the patient's condition. Pulse Transit Time (PTT) is the time it takes ECG pulses to travel from the heart to a sensor such as a sensor placed on the head, on a finger tip, or on the ear. PTT sensors can be in the mask, on sensors connected to the mask, or sensors used in conjunction with the mask. PTT measurements are used to determine patient arousal and qualitative blood pressure variation.

Thermal sensor 81 is used on the inside surface of the mask to detect nasal breathing. Thermal sensor 82 is used on the outside surface of the mask to detect oral breathing. The thermal sensitivity of the sensors 81 and 82 on the surface of the mask 10 opposite the nose or mouth indicates if the patient is breathing through his nose or mouth. The thermal sensors 81, 82 may alternatively be placed on the inside of the mask 10, on the outside of the mask 10, or inside of the material of mask 10 for detecting breathing. The thermal sensors 81, 82 may be a thermistor material, a thermocouple material or any other temperature sensitive material. The thermal sensors 81, 82 may be coatings on the inside of the mask, the outside of the mask or in the mask. The thermal sensors 81, 82 detect heat, which is proportional to the amount of breathing.

It is important to detect oral breathing for undetected or partially undetected oral breathing effects the integrity of the patient breathing gas breath monitoring and subsequently compromises the ideal gas delivery to the patient. It is important to detect mouth breathing to assist in diagnosis of sleep disordered breathing. Further, control of a mask nasal ventilation is effected by mouth breathing.

A pressure sensor 84 measures the pressure inside of the mask to indicate if there is positive pressure inside the mask. A pressure drop may indicate a leak.

A surface reflective oximetry sensor 85 on the inside of the mask detects the patient's pulse rate and oxygen saturation.

A surface blood pressure sensor 90 on the perimeter 12 of the mask 10 in contact with the patient can be used to monitor the patient's blood pressure.

A thermistor 91 on the perimeter 12 of the mask 10 in contact with the patient can be used to monitor the patient's temperature.

A patient recycled air detection system having a sensor 95 on the inside surface of the mask detects the amount expired air from the patient remaining in the mask 10. High levels of expired gas in the mask indicates the mask is not being flushed out and may lead to problems if not enough fresh gas is introduced.

A patient back gas occurrence detector 97 in the mask hose connector 14 detects the amount of expired gas in the mask returning with newly delivered gas.

Figure 7:
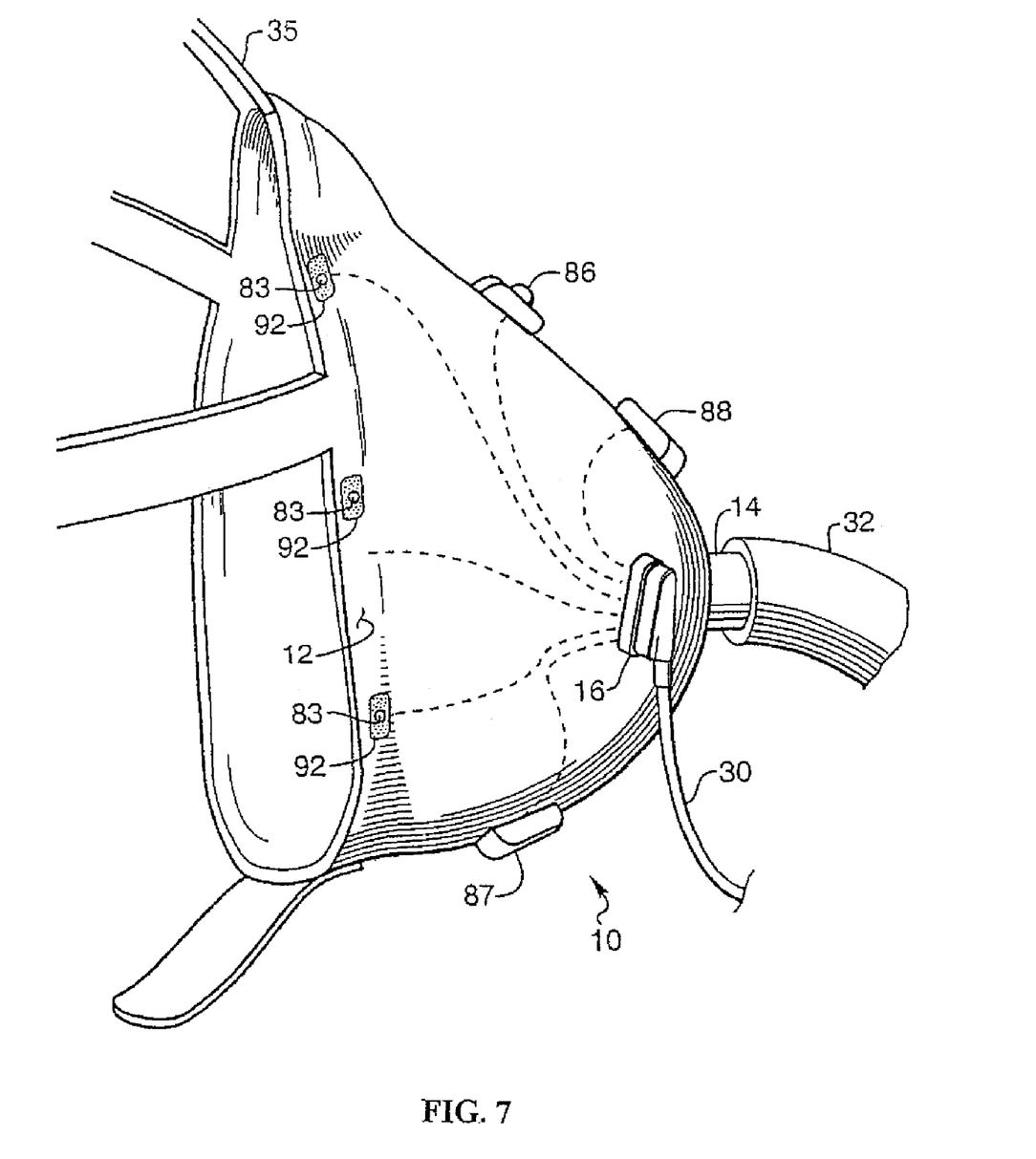
FIG. 7 shows a side schematic view of the mask with sensors on the surface of the mask.

FIG. 7 shows thermal sensors 83 such as thermistors or thermocouples on the inside or outside of the mask adjacent the perimeter 12. These sensors can be attached to a thermally conductive material 92 around the perimeter of the mask 10.

Alternatively the thermally conductive material may be on portions of the perimeter. This thermally sensitive material can be on the inside surface of mask 10, the outside surface of mask 10 or embedded within the mask material. Detection of a temperature change by thermal sensors 83 or thermal sensors 83 on thermally conductive material 92 correlates with mask leakage around the perimeter. The thermally sensitive material may be a thermally sensitive material in the mask on the inside of the mask, on the outside of the mask or on the perimeter of the mask. The thermally sensitive material may be a thermistor, a thermocouple, or any other thermally sensitive material.

Gases leaking from the mask 10 will cause a temperature change associated with the thermally conductive material 92 and sensors 83 and allow a healthcare specialist real-time monitoring of leak status or post monitoring status of mask leakage. In some instances this can be life saving where a patient's gas delivery is critical and in other cases the leakage incidence can assist in the diagnosis of a patient. This assistance may be in the form of alerting a health care specialist that the gas delivery was subject to leakage and this may affect patient treatment and patient diagnostic conditions. In other instances the gas leakage detection can allow the gas delivery system to automatically compensate for the gas leakage.

A light sensitive resistor 86 on the outside surface of the mask 10 indicates the ambient lighting conditions of the patient.

Position sensors 87 indicate position or activity of the patient. For example these sensors show if the patient is lying down and is motionless. Such a sensor may be a moving ball across switch contacts, or mercury sensor switches.

Body movement sensor 88 can be a PVD or piezo material or micro mechanical to detect the patient's body movements extent and rate to determine a wake versus rest state.

All of the above sensors may send data by telemetry rather than by cable 30. All of the above collected data may be used to monitor a patient for a variety of uses including sleep studies, anesthesia and sleep apnea.

The data collected can be converted to a serial data stream to allow a single wire to interface all the sensors. The sensors may provide data to adjust gas delivery to the patient.

Gain and filtering adjustments to the signals may be used to condition the signals close to source for optimal noise and signal performance. An electrical bias to sensors such as a patient position sensors, thermal conductive zones, microphones, or light dependent resistor may be applied.

A computer may process the data or simply store the data to from the monitoring sensors in the mask or straps attached thereto. The monitoring data may be used to diagnose a patient, provide feedback to machines attached to the patient, increase or decrease air supplies to a patient or perform other functions.

The mask 10 may be made such that it is a sterile disposable unit for medical use thus lowering costs of treatment by not needing to sterilize masks for new patients and providing a more sterile treatment than reusable masks.

In one embodiment, the present invention is utilized to control the delivery of a gas to a patient. An example of EEG data controlling in a bio-feedback application the delivery of gas to a patient may be when a patient has a nasal ventilation device such as a ventilator Continuous Positive Air Pressure (CPAP), Bi-Positive Air Pressure (BPAP), Variable Positive Air Pressure (VPAP), Sleep Linked Positive Air Pressure (SPAP) and the EEG electrodes provide one of the vital signs of if the patient is asleep. Gas is only applied to the mask when the patient is deemed to be asleep. The sensors in the mask 10 are better able to determine when the patient is actually asleep before applying assisted nasal ventilation. Premature application of pressure can prevent the patient from sleeping due to the added discomfort of positive pressure. This function is more sophisticated, sensitive to patient comfort than delay ramp systems commonly used on some ventilation systems.

Ventilation devices that use delay ramps do not take into account the patient's sleep state, and so these units are not able to adjust the application of gas to stages of deeper sleep when they are more tolerable to a patient. Furthermore, these units are also not able to adjust the applied pressure to levels which are better tolerated by the patient.

Figure 8:
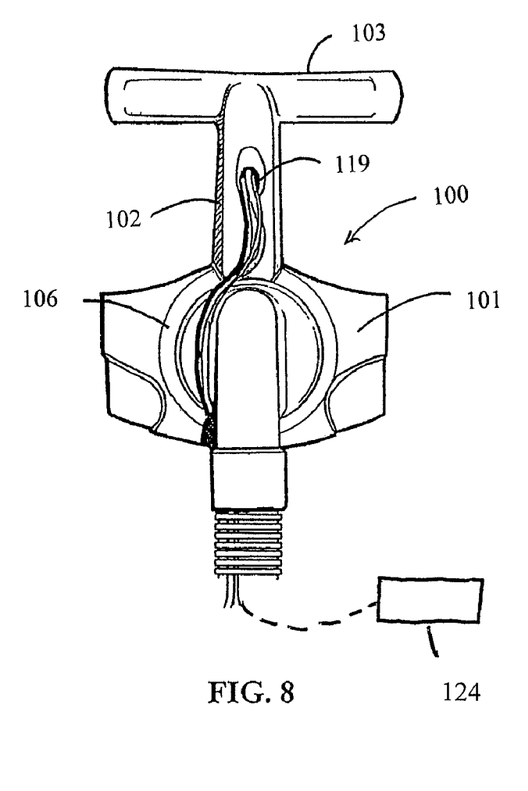
FIG. 8 shows a front elevated view of one embodiment of the subject invention.
Figures 9, 10:
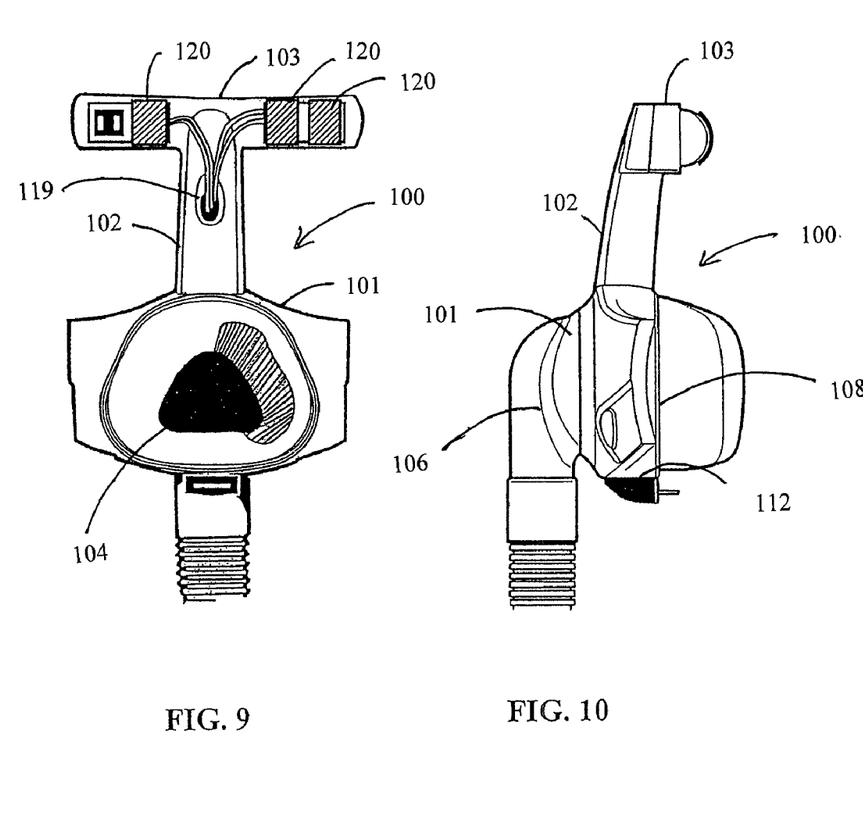
FIG. 9 shows a rear elevated view of the embodiment of FIG. 8.
FIG. 10 shows a side elevated view of the embodiment of FIG. 8.

As such, the inclusion of a bio feedback mechanism in the delivery of gas significant advantages. As shown in FIGS. 8, 9, and 10, in another embodiment, the present invention is adapted to provide bio-feedback that is utilized to control a gas delivery device. The embodiment is generally comprised of a mask assembly 100 having a body 101 and a forehead support 102 extending from the body. The body is comprised of an internal surface 104, an external surface 106, and a perimeter surface 108. The forehead support 102 extends upwardly from the body and is sized and shaped to contact a patient's forehead. The forehead support 102 includes a forehead support bar 103 adapted to contact a patient's forehead.

Figure 11:
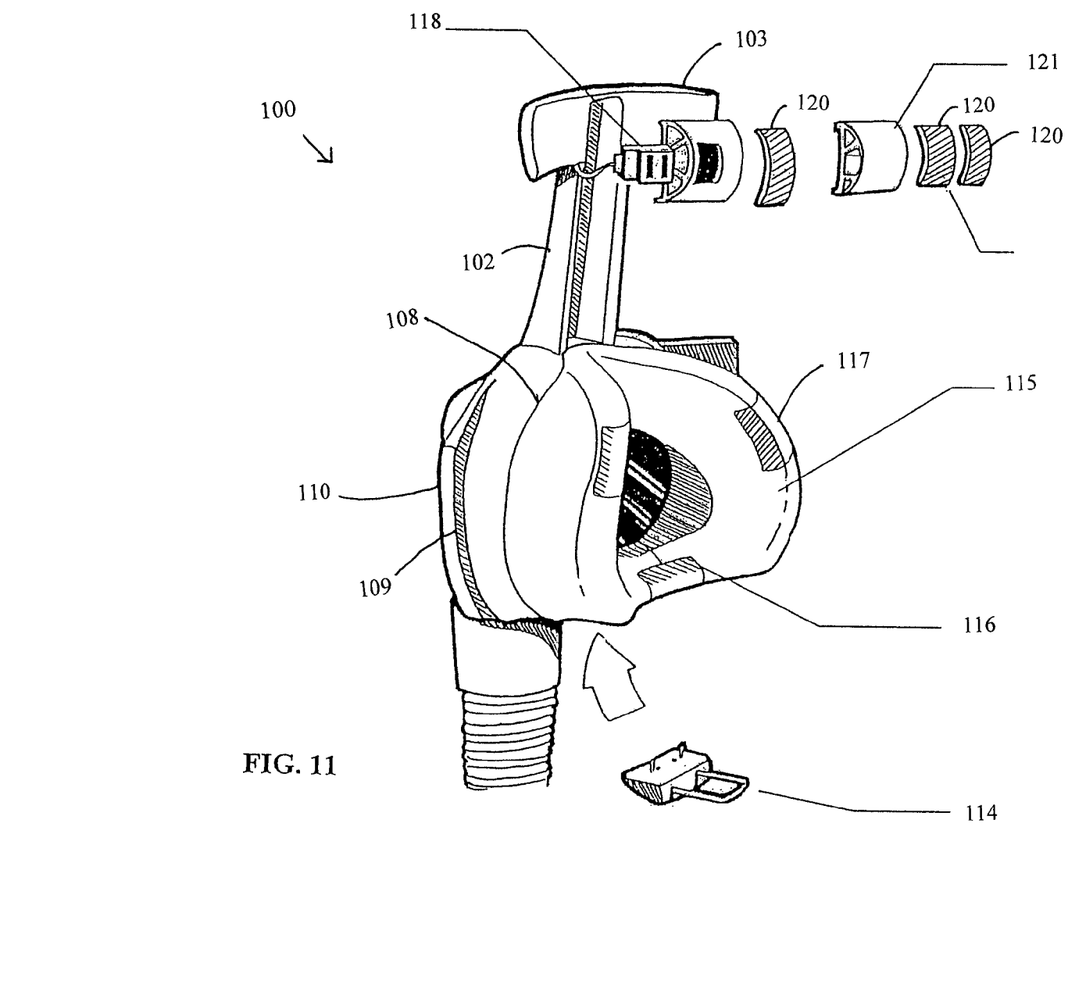
FIG. 11 shows an exploded view of one embodiment of the subject invention.
Figure 12:
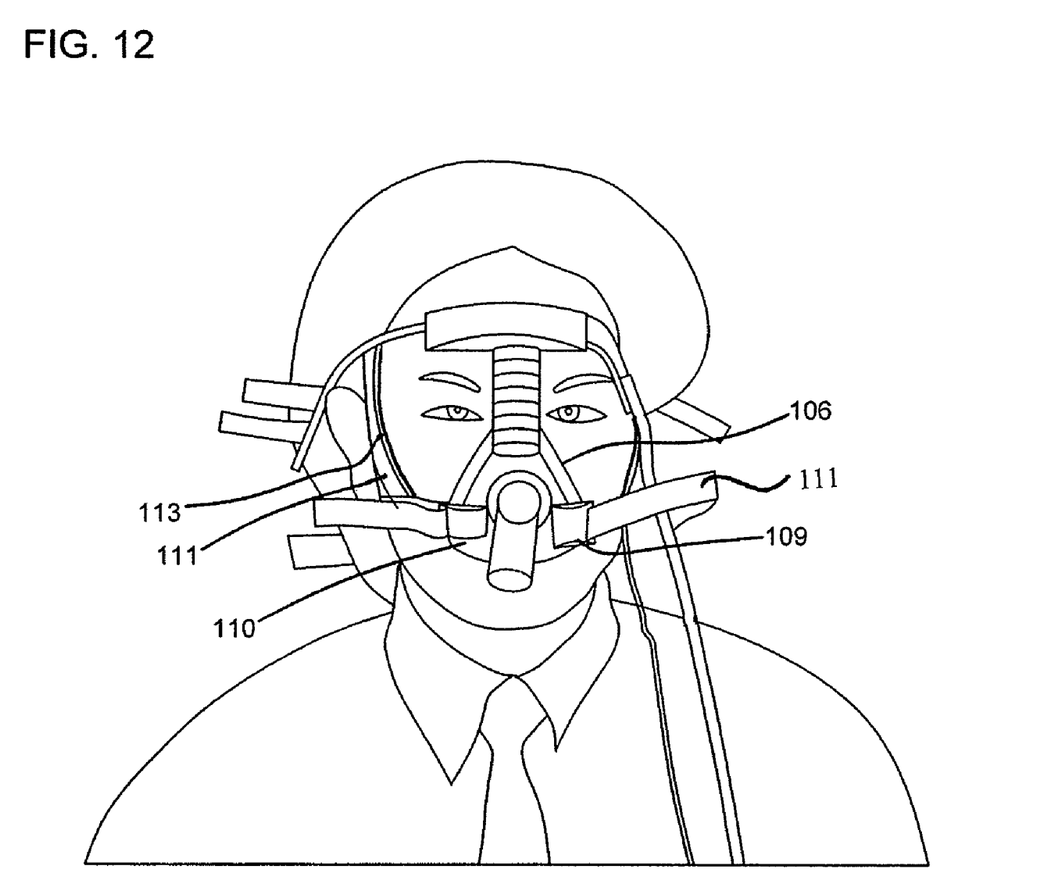
FIG. 12 shows a front view of one embodiment of the subject invention, as applied to a patient.

As shown in FIGS. 11 and 12, in one embodiment, the body 101 includes wings 110 extending from the external surface 106. The wings 110 include an attachment surface 109 serving as a point of attachment to mask straps 111. Conductive carbonized silicon rubber padding 113 are positioned along the strap to detect EEG signals. The external surface 106 also includes a sensor seat 112 wherein a thermistor 114 is detachably connected.

In one embodiment, the perimeter surface 108 has cushioning 115 extending therefrom. The cushioning 115 is preferably made a silicon plastic material and is sized and shaped to form an effective seal around a patient's nose. It is also contemplated of shaping the mask to conform to the entire nasal and oral region like general breathing masks. A thermistor coating 116 is placed on the cushioning in order to detect temperature gradient differences indicative of a leak in the mask. The cushioning 115 may also include conductive surfaces 117 to detect physiological signals such as ECG signals. The cushioning 115 provides a comfortable seal around a patient's nose, while reducing the possibility of creating facial sores generally attributed to the metallic sensors used in the prior art.

As shown in FIGS. 8, 9, and 11, in one embodiment, the forehead support 102 includes a forehead support bar 103 which extends generally perpendicular to the rest of the forehead support 102. The forehead support bar 103 acts to stabilize the mask 100 on the patient's face and to position sensors along the patient's forehead. A pulse oximetry sensor 118 and EEG sensors 120 are connected to the forehead support bar 103. The forehead support 102 also includes a channel 119 wherein leads from the various sensors travel through.

In one embodiment, the EEG sensors 120 includes a conductive carbonized silicone rubber padding 122 which provides cushioning for the forehead support bar and a conductive surface for detecting EEG waves. A support 121 stabilizes contact between a patient's forehead and the EEG sensors 120. The forehead support bar 103 positions the EEG sensors 120 on a patient's forehead just below standard electrode placement positions FP1 used for an EEG channel and FP2 used for a patient ground. The positioning of the EEG sensors on the patients forehead enables the mask to take relevant EEG readings.

One or more oximetry sensors or pulse-wave sensors may be positioned on the forehead stabilizer pads 103 of the breathing mask utilized, for example, in nasal positive air pressure systems, patient oxygen therapy, or ventilator breathing masks. Electrophysiological sensors including (but not limited to) sensors enabling the investigation of sleep and breathing-related sleep disorders such as electromyography (EMG), electroencephalography (EEG), electrooculography (EOG) and electrocardiography (ECG), may be embedded in the forehead stabilizer pads 103 of a breathing mask, such as a nasal positive air pressure, patient oxygen therapy, or ventilator breathing mask (but not limited to).

This capability can enable the monitoring or derivation of pulse transit time (PTT), PTT-derived arousals, pulse arterial tone (PAT), pulse wave amplitude (PWA), respiratory effort related arousals (RERA) for diagnosis or treatment countermeasure purposes, both in real-time or post monitoring.

One or more sensors can be separated with non-conductive barriers between each respective sensor to enable a number of appropriately placed sensors to be positioned within the mask forehead stabilizer pads 103.

Electrophysiological sensors including (but not limited to) sensors enabling the investigation of sleep and breathing-related sleep disorders such as electromyography (EMG), electroencephalography (EEG), electrooculography (EOG) and electrocardiography (ECG), embedded in the face seal of the breathing mask, or embedded as (such as but not silicon, rubber, plastic or other flexible material), including carbon impregnated silicon or rubber forming a near perfect seal but containing an effective conductive interface between the breathing mask seal and the subject's face.

One or more sensors can be separated with non-conductive barriers between each respective sensor to enable a number of appropriately placed sensors to be positioned within the mask seal perimeter. In this way a means is enabled, for example (but not limited to) for cheek EMG to be detected (with a pair of sensors separated but appropriately located to detect the subjects cheek EMG signal (this signal declines in electrical activity as a subject transitions into deeper stages or sleep, until the lowest cheek EMG activity during REM sleep), EOG (detectable via conductive zones around the upper nose bridge section and near the subjects eyes), EEG (frontal EEG and arousals also detectable from nose or top of mask conductive perimeter zone, for example). Oral breathing detection material including thermally conductive polymer or material (such as but not silicon, rubber, plastic or other flexible material) impregnated or embedded, or attached to inside or particularly outside surface of breathing mask, enabling detection of nasal and or oral (via subject's mouth) breathing, respectively. Detection of oral breathing can be very important with nasal gas delivery such as a nasal positive air pressure, patient oxygen therapy, or ventilator breathing mask (but not limited to) due to the fact that if this breathing goes undetected (as in previous art nasal masks) then the optimal therapy control delivery to the subject is compromised (the device delivering the gas underestimated the actual breathing depth or volume of the subject due to the undetected breathing "leakage" via the mouth.

Mask seal leakage detection can be detected by using thermally conductive polymer or material ((such as but not silicon, rubber, plastic or other flexible material) impregnated or embedded, or attached to inside or particularly outside surface of breathing mask face seal. By positioning thermally sensitive material in one or more zones around the face seal it is possible to detect and compute the amount of leakage experienced by the subject receiving gas delivery therapy. The information derived from such "leakage" enables more accurate and precise computation of the therapy devices gas delivery requirements to counter the actual breathing stress, sleep disorders or other health conditions being treated by the gas deliver system. Detection of mask perimeter leakage can be very important with nasal gas delivery such as a nasal positive air pressure, patient oxygen therapy, or ventilator breathing mask (but not limited to) due to the fact that if this breathing goes undetected (as in previous art nasal masks) then the optimal therapy control delivery to the subject is compromised (the device delivering the gas underestimated the actual breathing depth or volume of the subject due to the undetected breathing "leakage" via the mouth.

Patient position sensor-breathing can be highly effected by patient position (upright, lying on back, left-side, right side, for example). The integration of a position sensor within the mask can also allow transmission of valuable data for improved gas delivery decision and control.

Typically, data sampling for the EEG sensor is set to 16 bit and 512 samples per second. Preferably, unfiltered EEG data received from the EEG sensors 120 are high pass filtered and low pass filtered to 0.15 Hz and 200 Hz, respectively.

As shown in FIG. 12, in one embodiment, EMG electrodes 125 are integrated on the mask straps 111. The EMG electrodes 125 are comprised of soft cushions of conductive carbonized silicon rubber. The EMG electrodes are positioned on the mask straps so that when the mask is applied to a patient, the EMG sensors are positioned over the masseter muscle (cheek) and A1, for the EMG channel data and the reference, respectively. The positioning of the EMG electrodes with respect to the patient enables the present invention to monitor muscle activity which are indicative of sleep disorder breathing and of arousal.

In one embodiment, the EMG electrodes 125 are data sampled at 512 samples per second. The EMG signals are typically high pass and low pass filtered at 70 Hz and 200 Hz, respectively.

The location of the pulse oximetry sensor 118 on the forehead support bar 103 enables the present invention to take accurate oximetry readings using a unique reflective oximetry techniques. The pulse oximetry sensor 118 includes an LED light and a light sensor. The LED beams light through the forehead skin and to the skull. The light bounces of the skull and is reflected back to the light sensor which in turn converts the light into an analog signal. The analog signal is then high pass filtered at about 0.01 Hz and is then analyzed using known pulse oximetric techniques to determine SPO2 levels, a pulse plethysmography waveform, and a heart rate.

In one embodiment, the subject mask assembly 100 is in communication with a control system 124 for a gas delivery device. One such control system is described in U.S. Pat. No. 6,397,845 to Burton, the contents of which are hereby incorporated by reference in its entirety. The control system 124 is adapted to determine a sleep state of a patient from the physiological signals which are being detected by the mask assembly 100. The patient's sleep state is then used as a determinate for controlling the delivery of gas to the patient.

One of the sleep states detected in U.S. Pat. No. 6,397,845 is the state of arousal. Arousals usually do not cause a person to wake up, but they often transition a patient away from deeper stages of sleep. Furthermore, arousals are often followed by a relatively long period before reentering deeper stages of sleep such as REM or slow-wave. As a result, a person who has numerous arousals may experience fragmented sleep which in turn causes excessive daytime sleepiness or other symptoms.

In one embodiment, arousal is determined using Pulse Transit Time (PTT). Studies have shown that sleep disorders such as apnea, hypopnea or upper airway resistance result in an accompanying arousal, and this arousal is accompanied by changes in heart rate, a transient burst of sympathetic activity, and a surge in blood pressure. Obstructive sleep apnea can be correlated with an obvious and measurable increase in intrathoracic pressure associated with obstructive effort and cardiobalistogram effect. The cardiobalistogram effect is created when the lungs apply pressure to the heart. This compresses the heart and reduces the volume of blood pumped by the heart. These cardiovascular changes are recognizable by way of a transient but significant dip in the patient's baseline PTT value.

PTT is the time taken for the pulse wave to travel between two arterial sites. The blood pressure is directly proportional to the speed that the arterial pressure wave travels. A rise in blood pressure relates to faster pulse wave and thus shorter PTT. Conversely, a drop in blood pressure results in a slowing of the pulse wave and an increase in PTT.

In one embodiment, PTT is obtained directly by utilizing sensors located on the present invention. A detector receives input from the mask and generates a plethysmography waveform. A second detector receives input from the mask and generates an ECG signal. The waveform and the signal are inputted into the control system and a PTT reading is calculated.

The PTT is derived by utilizing a plethysmography waveform obtained by using pulse oximetry readings obtained from the pulse oximetry sensor 118 in combination with an ECG signal detected along the perimeter surface 108. The ECG R or Q wave can be used as the start point for the PTT measurement and the end point of the PTT measurement can be the point representing 25% or 50% of the height of the maximum pulse wave value from the pulse oximetry sensor 118.

The control system 124 can also be utilized to control delivery of medications and anesthetic agents to a patient. In such a configuration, the control system is typically in communication with a drug dispensing apparatus such as an infusion pump.

The matter set forth in the foregoing description and accompanying drawings is offered by way of illustration only and not as a limitation. While a particular embodiment has been shown and described, it will be obvious to those skilled in the art that changes and modifications may be made without departing from the broader aspects of applicants' contribution. The actual scope of the protection sought is intended to be defined in the following claims when viewed in their proper perspective based on the prior art.

The invention claimed is:

1. A mask assembly comprising:
   a body having an internal surface, an external surface, and a perimeter surface; and
   a forehead support connected to the body;
   a support bar connected to the forehead support and extending in generally lateral directions from the forehead support to define a pair of sensor sites on said forehead support, with one of the pair of sensor sites being proximate to a FP1 standard electrode placement position of a patient and the other of the pair of sensor sites being proximate to a FP2standard electrode placement position of said patient;
   a pair of EEG sensors at ends of said support bar, with one of the pair of EEG sensors being held by the support bar at said FP1 standard electrode placement position and the other of the pair of EEG sensors being held by the support bar at said FP2 standard electrode placement position;
   a control system adapted to receive a signal from said pair of EEG sensors, said control system determining said patient's sleep stage based at least in part on said signal; and
   a gas delivery device in communication with said control system, wherein said control system is adapted to adjust a gas delivery setting based upon a control system determination of said patient's sleep stage, such that said gas delivery device delivers gas to the patient based on the control system determination of said patient's sleep stage.

2. The assembly of claim 1, wherein the perimeter surface includes a padding material having a thermosensitive coating.

3. The assembly of claim 1 wherein wires connected to said pair of EEG sensors pass through an aperture of said support bar forehead.

4. The assembly of claim 1, and wherein an SPO2 sensor is located on the forehead support bar.

5. The assembly of claim 1, wherein the pair of EEG sensors includes pads comprised of a conductive carbonized rubber material.

6. The assembly of claim 1, and further comprising a strap extending from the mask, and wherein a physiological sensor is located on the strap.

7. The assembly of claim 5, wherein a portion of the pads is adapted to measure EOG.

8. A gas delivery system comprising:
a mask comprising a mask body having an internal surface, an external surface, and a perimeter surface;
a forehead support extending from the body and adapted to contact a forehead surface of a patient during use, a support bar connected to the forehead support and extending in generally lateral directions from the forehead support to define a pair of sensor sites at ends of said support bar, with one of the pair of sensor sites being proximate to a FP1 standard electrode placement position of said patient and the other of the pair of sensor sites being proximate to a FP2 standard electrode placement position of said patient;
a pair of EEG sensors, with one of the pair of EEG sensors being held by the support bar at said FP1 standard electrode placement position and the other of the pair of EEG sensors being held by the support bar at said FP2 standard electrode placement position;
a gas delivery device having an adjustable gas delivery setting; and
a control system in communication with the gas delivery device and the pair of EEG sensors, the control system adapted to determine a sleep stage of the patient and to adjust a gas delivery setting based upon a determined sleep stage.

9. The system of claim 8, further comprising a EMG sensor at said support bar.

10. The system of claim 8, further comprising a ECG sensor at said support bar.

11. The system of claim 10, and further comprising a SPO2 sensor connected to the mask.

12. The system of claim 8, wherein wires connected to said pair of EEG sensors pass through an aperture in said support bar.

13. The system of claim 8, wherein the control system is also adapted to determine patient arousal.

14. The system of claim 8, wherein the control system determines arousal by calculating PTT values from a SPO2 reading and a ECG reading.

15. The system of claim 8, wherein the control system determines arousal by analyzing cortical and subcortical EEG signals.

16. The system of claim 8, wherein the control system is provided in communication with a cardiac pacemaker, said control system being adapted to adjust the gas delivery based on a signal from the cardiac pacemaker.

17. A method of delivering gas comprising:
providing a mask adapted to detect an EEG signal and to deliver a gas, the mask comprising a mask body having an internal surface, an external surface, and a perimeter surface;
providing a forehead support extending from the body and adapted to contact a forehead surface of a patient during use, the forehead support having a plurality of sensors located thereon for detecting electrophysiological signals of the patient, with at least one of said plurality of sensors being a first EEG sensor positioned proximate to a FP1 standard electrode placement position of said patient and a second of said plurality of sensors being a second EEG sensor positioned proximate to a FP2 standard electrode placement position of said patient;
providing a gas delivery device in fluid communication with the mask and having an adjustable gas output;
determining a sleep stage from EEG signals detected by the mask; and
adjusting the output from the gas delivery device based on the sleep stage, by the use of a control system adapted to adjust a gas delivery setting based upon a determined sleep stage.

18. The method of claim 17, wherein said determining a sleep state includes determining arousal.

19. The method of claim 18, wherein said determining arousal includes calculating PTT values from a SPO2 reading and a ECG reading of the patient.

20. The method of claim 18, wherein determining arousal includes analyzing cortical and subcortical EEG signals of the patient.

21. The method of claim 17, wherein a processor is provided in communication with the gas delivery device and a cardiac pacemaker, said processor being adapted to adjust the gas delivery based on a signal from the cardiac pacemaker.

* * * * *